United States Patent [19]

Allen et al.

[11] Patent Number: 5,026,159
[45] Date of Patent: Jun. 25, 1991

[54] AREA-MODULATED LUMINESCENCE (AML)

[75] Inventors: Fritz S. Allen, Corrales; Carlos Bustamante; Thomas M. Niemczyk, both of Albuquerque, all of N. Mex.; Burton P. Dorman, Berkeley, Calif.

[73] Assignee: Acrogen, Inc., Oakland, Calif.

[21] Appl. No.: 354,137

[22] Filed: May 19, 1989

[51] Int. Cl.⁵ .............................................. G01N 21/64
[52] U.S. Cl. .................................. 356/318; 250/458.1; 356/417
[58] Field of Search ....................... 356/317, 318, 417; 250/365, 458.1, 459.1, 461.1, 461.2

[56] References Cited

U.S. PATENT DOCUMENTS

| | | | |
|---|---|---|---|
| 4,030,827 | 6/1977 | Delhaye et al. | 356/318 |
| 4,320,970 | 3/1982 | Dowben et al. | |
| 4,407,964 | 10/1983 | Elings et al. | |
| 4,421,860 | 12/1983 | Elings et al. | |
| 4,461,573 | 7/1984 | Lucht et al. | |
| 4,501,970 | 2/1985 | Nelson et al. | |
| 4,537,861 | 8/1985 | Elings et al. | |
| 4,631,581 | 12/1986 | Carlsson | 356/318 |
| 4,647,544 | 3/1987 | Nicoli et al. | |
| 4,750,837 | 6/1988 | Gifford et al. | |
| 4,943,159 | 7/1990 | Oetliker et al. | 356/417 |

OTHER PUBLICATIONS

Nguyen et al., "Detection of Single Molecules of Phycoerythrin in Hydrodynamically Focused Flows by Laser-Induced Fluorescence", in *Anal. Chem.* (1987), 59:2158-2161.

Mathies and Stryer, "Single-Molecule Fluorescence Detection: A Feasibility Study Using Phycoerythrin", in *Applications of Fluorescence in the Biomedical Sciences* (1986), pp. 129-140.

Bustamante and Maestre, "Statistical Effects in the Absorption and Optical Activity of Particulate Suspension", in *Proc. Natl. Acad. Sci. USA* (1988), 85:8482-8486.

Dovichi et al., "Attogram Detection Limit for Aqueous Dye Sample by Laser-Induced Fluorescence", in *Science* (1983), 219:845-847.

Nguyen et al., "Ultrasensitive Laser-Induced Fluorescence Detection in Hydrodynamically Focused Flows", in *J. Opt. Soc. Am. B* (1987), 4(2):138-143.

Primary Examiner—F. L. Evans
Attorney, Agent, or Firm—Bertram I. Rowland

[57] ABSTRACT

A luminescence measuring system is provided for detecting luminescence at extremely low concentrations of luminescing moieties. The method employs alternating radiation at a plurality of loci of an inhomogenous solution, where the radiant power is maintained constant, and the irradiated volumes of pairs of loci are systematically varied. With the probability being very low that the same luminescence signal will be obtained in the two or more measurements, by comparing the measurements, one can detect a low luminescence signal in the presence of relatively high noise levels. Various techniques are described for modulating the irradiance and detecting changes in signal.

6 Claims, 2 Drawing Sheets

AREA-MODULATED LUMINESCENCE (AML)

INTRODUCTION

1. Technical Field

The field of this invention is related to high detectability measurements of luminescence.

2. Background

The world has become increasingly dependent on the ability to measure a wide variety of analytes in an increasing number of different contexts. Qualitative and quantitative techniques, involving different chemistries or different instrumentation is used in medicine, process control, detection of pollutants, monitoring of systems, and the like. The concentration of the substance of interest or "analyte," the presence of interfering materials, ease of isolation and pretreatment of the sample, are only a few of the concerns involved with a measurement. The preparation of the sample is only the prelude to the detection of the analyte.

In many contexts, it is desirable to have minimum pretreatment of the analyte. With microorganisms, because of the presently low sensitivity of instrumentation, it is frequently necessary to grow the microorganisms present in a sample, so as to amplify their number to allow for detection. In other situations, such as the use of blood, various components in the blood may interfere with a number of detection systems, due to the presence of fluorescent materials, enzyme inhibitors, or the like. Because of the interest in minimizing pretreatment, shortening the time for a determination, and reducing background interference, there is substantial interest in being able to greatly increase the sensitivity of the detection system, so one could detect very small numbers of analytes in a sample.

Fluorometry has been the subject of numerous investigations for increasing sensitivity and the ability to accurately measure low concentrations or low numbers of analyte molecules. However, fluorometry suffers from many disadvantages, in that substantial background values may be encountered, due to the presence of fluorescent molecules in the sample, Rayleigh scattering, Raman scattering and the like or noise in the signal or background may be encountered due to various sources, including variations in the irradiation level of the light source. While there has been substantial improvement in the ability to reduce interference from many of these contributors to the noise level, nevertheless there still remains opportunities for improvement.

Relevant Literature

U.S Patents of interest include U.S. Pat. Nos. 4,320,970, 4,407,964, 4,421,860, 4,461,573, 4,501,970, 4,531,834, 4,537,861, 4,647,544 and 4,750,837. Articles of interest associated with the use of fluorometry in the measurement of analytes at low concentrations include Dovichi, et. al., *Science* 19:845–847, 1983; Mathies and Stryer, "Single-Molecule Fluorescence Detection: A Feasibility Study Using Phycoerythrin," *Applications of Fluorescence in the Biochemical Sciences*, pp. 129–140, 1986; Nguyen and Keller, "Ultrasensitive Laser-induced Fluorescence Detection in Hydrodynamically Focused Flows, *J. Opt. Soc. An. B.,* 4:No.2, February 1987, pp.138–143; Nguyen, et. al., *Anal. Chem.,* 1987, 59:2158-2161; and Bustamante and Maestre, *Proc. Natl. Acad. Sci. USA.,* 85:8482-8486, 1988.

SUMMARY OF THE DISCLOSURE

Instruments and methods are provided to detect low levels of luminescence. The system relies on using constant incident radiant power over two different loci in a sample that is usually of constant depth, where there is a low probability of finding the same concentration of light emission during the time of detection at the two loci. Repetitive measurements can be made and averaged. Various techniques are employed for changing the size or position of the irradiated loci. By processing the information from the two loci, small numbers of analytes may be detected and quantitated.

DESCRIPTION OF SPECIFIC EMBODIMENTS

Figure 1:
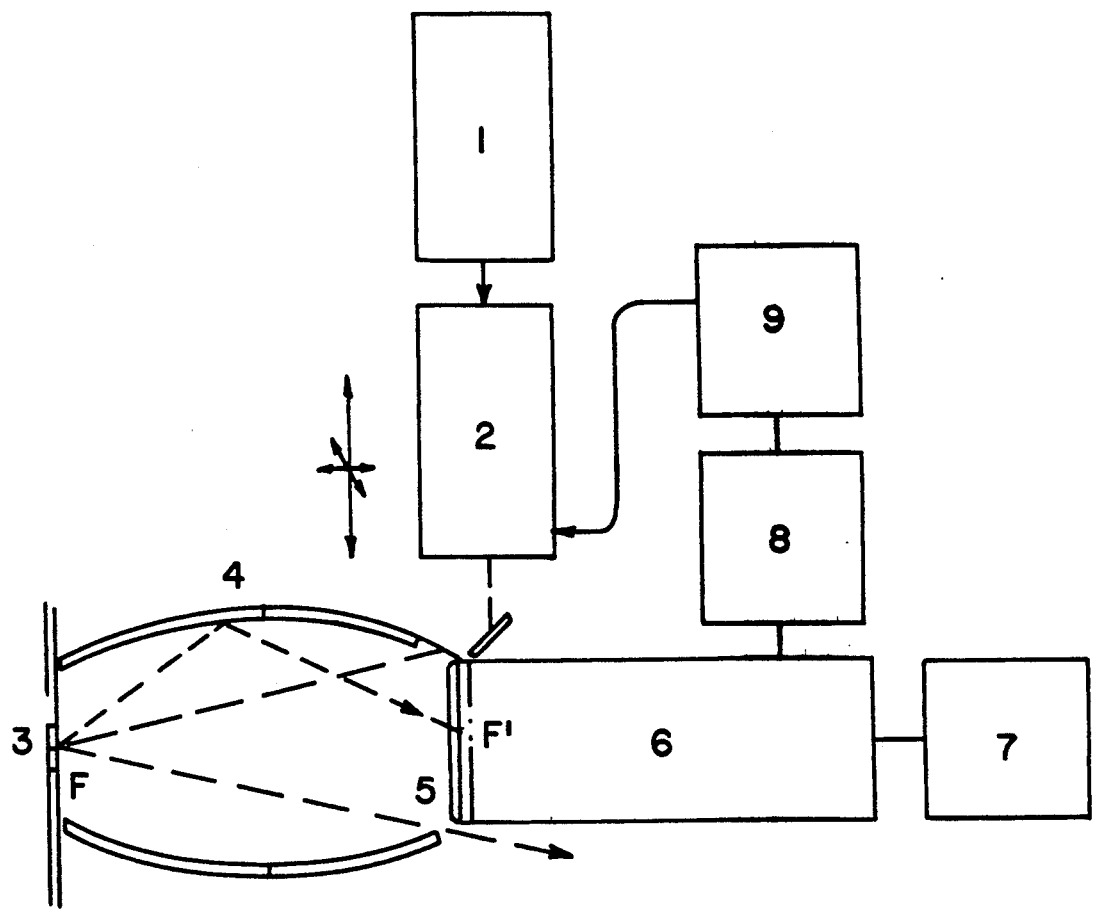
FIG. 1 is a schematic drawing of the subject apparatus.

Fluorometric or phosphorometric systems are provided for detecting low levels of analytes by irradiating loci with a fixed photon flux, where the volume of the loci is selected so as to minimize the probability that the chromophore concentration in two or more different loci will be the same. The maximum volume will be selected so that there will be a high probability that there will be at least 1 particle in an irradiated locus. The subject method will therefore be directed primarily where the measurement is of concentrations of less than about 0.1 nM, usually less than about 1 pM (picomolar), preferably less than about 1 fM (femtomolar) and the system may detect analytes at concentrations of less than about 1 aM (attomolar) or even less.

The subject method is referred to as Area Modulated Luminescence (AML). Luminescence is intended to include both phosphorescence and fluorescence, where the latter will usually be employed. The subject method is predicated on the fact that at ultra-low concentrations, the analyte will be inhomogenously distributed throughout the analytical sample and these samples will not obey the Beer-Lambert law. A property of such samples is the existence of regions within the analytical sample that are substantially devoid or depleted of analyte.

The distinction between homogeneously distributed background and inhomogeneously distributed analyte can be exploited to lower the detection limit for analyte using AML. The AML technique is intrinsically directed toward detectivity as a fundamental objective. This orientation toward detection of analyte distinguishes AML from prior analytical spectrometric methods. However, AML methods, coupled with knowledge of measurement volumes and fluctuation theory can be employed to determine bulk analyte concentration.

The subject method is particularly useful where there exists a large degree of inhomogeneity with respect to the number of analyte molecules in the measurement volumes. Applications include, for example, when the analyte can be aggregated into a small number of loci in the analytical sample, as particles, cells, cell fragments, organelles, or the like. Also, the subject method finds use where a luminescent moiety becomes bound to a large object, such as a cell, where the unbound luminescent moiety remains in solution. In addition, the subject method finds use in detecting nucleic acid strands, for example, where a plurality of luminescent moieties may be brought together by hybridization with a target sequence. The most unique and powerful applications involve the detection of analyte at ultra-low concentrations.

For understanding the subject invention, comparison between the nature of the subject measurements and conventional absorption and luminescence spectroscopy is considered of value. In conventional photoluminescence measurements, the luminescence signal is proportional to the radiant power (energy per unit time) absorbed by the specimen. The radiant power (photons/sec) absorbed by any specimen depends on (1) the incident radiant power on the specimen and (2) the total number of absorbers that interact with the light beam. The incident radiant power is equal to the product of the irradiance (power per unit area) and the irradiated area of the sample. For a given area of illumination, the number of absorbers that interact with the incident light depends on the thickness of the medium and the concentration of the absorbing species. Photoluminescence measurements are usually conducted under such circumstances (e.g., relatively low concentration, or short path lengths, etc.) that the absorbed radiant power and the luminescence signal are linearly related to incident radiant power, to sample thickness and to analyte concentration.

It is understood that the number of analyte molecules in any volume element of a given specimen is subject to statistical fluctuations; the magnitude of such fluctuations is of the order of the square root of the number of analyte molecules. Therefore, when analyte is present at sufficiently high concentration, the statistical fluctuations represent a small enough fraction of the analyte concentration that the medium can be treated as if it contained a statistically significant mean concentration of analyte per unit volume. Such specimens may be treated to a good approximation as a homogeneous continuum. This homogeneity, and the concentration and path length dependence are necessary conditions of the Beer-Lambert absorption law that underlies conventional absorption and luminescence spectroscopy. Conventional analytical fluorometry and spectrofluorometry using state-of-the-art spectrofluorometers offer detection limits for analytes in solution at concentrations as low as $10^{-12}$ to $10^{-13}$ M, corresponding to about $10^9$ to $10^8$ particles per milliliter.

Specimens containing ultra-low concentrations of analyte cannot be treated as a homogeneous continuum. When analyte is present at ultra-low concentrations, the luminescence signal derived from the analyte is no longer simply related to the concentration and sample thickness. On the other hand, non-analyte components of the analytical sample, especially the solvent, will be present at very much higher concentrations. Consequently, the solvent and any concomitant molecular species that are present at concentrations substantially higher than the analyte may be treated as if they are continuously and homogeneously dispersed in the sample.

The AML technique consists of any spectrometric method that exploits modulation of the illuminated sample area. Although modulation may be achieved in various experimental modes, it is experimentally convenient to keep optical path length and the photon flux constant. In each mode, the key is to measure the small difference in luminescence output that accompanies area modulation.

The luminescence difference signal is extracted from the background signal. Scattered photons, such as Rayleigh and Raman can be discriminated against by time or wavelength domain technologies. Background luminescence photons and scatter photons come principally from materials that are homogenously distributed and therefore may be discriminated against by the subject methodology. Consequently, a small differential signal that is generated by the analyte in the subject technique can be directly observable, especially if the measurement is conducted in a cyclic fashion.

If the irradiated area is modulated in a regular, repetitive way, thereby changing the irradiance with or without changes in the spatial locus, even very small signals can be resolved. In order for a signal in the subject invention to be directly observable, it must be significantly larger than the fluctuations in the background signal. By employing a cyclic system, the signal from the analyte plus background need only be on the average marginally above that of the background signal alone. The extent of the increase required depends on the number of cycles available for observation. Such techniques such as gated integration techniques, photon counting, autocorrelation, and synchronous detection may be employed individually or in combination, in order to extract small regular variations from large background contributions. See U.S. Pat. No. 4,407,964.

While not intending to be bound by any theoretical analysis, the theory of measurement underlying all modes of AML, can be understood in terms of a simple formalism. Consider the (idealized) experimental situation in which N photons per second, usually of fixed wavelength, are incident upon (illuminate) the detection volume V of cross-sectional area A and depth (optical path length) d. Notice that N, the photon flux, when multiplied by the energies of the photons, gives the incident radiant power of the beam. Once the energies of the photons are defined, then photon flux and radiant power can be used interchangeably without modifying the conceptual framework of the description. Let n be the number of a given molecular species contained in V and capable of interacting with incident light. Let the effective cross section for luminescence be $\sigma$ per interacting molecule (where $\sigma$ represents the product of the molecular cross-section for absorption and for re-emission of a luminescence photon). Then the effective total interaction cross-section is given by the sum of the cross-section of the n interacting molecules; i.e., the product $n \times \sigma$. And the expected number/sec of luminescence photons, L, is given as $$L = \frac{n\sigma}{A} \cdot N \qquad (i)$$

where the fractional term is simply the ratio between the effective interaction cross-section $n\sigma$ and geometric cross-sectional area A. [Notice that the stated proportionality between L and N necessarily implies that the incident photon flux, N, is "non-saturating" and that the population of the interacting species is constant, i.e., not being depleted. Circumstances under which one or both of these assumptions do not hold will be examined.]

Inasmuch as the AML technique involves the modulation of area, we examine the effect on L of changing A while the photon flux, N, is held constant. The area can be modulated by changing the magnitude of the illuminated area about a fixed point, by changing the location of an illuminated area of fixed magnitude, or both. But sample depth, d, is constrained to be fixed. Let us examine the effect on n and, in turn, on L. In general, $n=\rho V$ where $\rho$ is the density (number per unit volume) of interacting species. If $\rho$ is fixed (a constant), as would be the case for homogeneously distributed species, then:

$$L = \frac{n\sigma}{A} \cdot N = \frac{\rho V \sigma}{A} \cdot N = \frac{\rho \sigma A d}{A} \cdot N = \rho \sigma d \cdot N \quad \text{(ii)}$$

The result is that the illuminated area A divides out of the expression for L; i.e., L does not change with area (or, at constant path length d, with volume) for any species where $\rho$ is fixed. This means that the luminescence signal will not change with changes in the area illuminated for any species that is homogeneously distributed in the analytical specimen.

More generally if $\rho$ is not fixed, i.e., if the interacting species is not assumed to be homogeneously distributed, then n will not necessarily vary in proportion to volume. In this case, as V goes to V', $n = \rho V = \rho A d$ may change to $n' = \rho' V' = \rho' A' d$. Then from (i)

$$L' = \frac{n'\sigma}{A'} \cdot N = \frac{\rho' A' d \sigma}{A'} \cdot N = \rho' \sigma d \cdot N. \quad \text{(iii)}$$

The difference signal, $\Delta L$, is obtained by subtracting Equation (ii) from Equation (iii), yielding $$\Delta L = L' - L = (\rho' - \rho)\sigma d \cdot N \quad \text{(iv)}$$

We see that $\Delta L = 0$ if and only if $\rho' = \rho$, i.e., if the density (number per unit volume) of the interacting species is the same in V' as in V, i.e., if the species is homogeneously distributed. Otherwise, for non-homogeneously distributed species, i.e., if $\rho'$ does not equal $\rho$, then $\Delta L$ does not equal 0. That is, if $\rho = \rho(V)$, then $\Delta L$ does not equal 0 and a non-zero difference signal will be produced if the area volume/d) is modulated.

Note that for A expressed in cm², the quantity N/A represents the irradiance expressed in photons per cm² per second. Therefore the modulation of area at constant radiant power corresponds to a change in irradiance. This particular embodiment of AML, especially when the luminescence is in the form of fluorescence, may be designated Differential Irradiance Fluorometry (DIF). DIF is novel in that the illumination optics are deliberately designed to produce sample irradiance that varies in the course of the measurement.

The preceding description includes certain features that are illustrative and that may be experimentally advantageous but that should not be considered limiting. For example, embodiments may be envisioned in which experimental parameters such as the photon flux, N, or the sample thickness, d, instead of being held constant could, with proper normalization, be allowed to vary, as in the case of a rotating mask system or a wedge-shaped sample.

As noted above, the preceding analysis needs to be modified to account for certain "special" cases. One such case exists when the irradiating photon flux is sufficient to "saturate" the capability of the interacting species to absorb and emit luminescence. Saturation occurs when the ground state population is reduced to the point that an increase in incident photons does not result in any further increase in luminescence. In this situation the luminescence, $L_{sat}$, from a saturated species is independent of incident irradiance and is simply proportional to the number of saturated molecules, $n_{sat}$.

That is, No/A becomes effectively a constant, k, the rate constant for deactivation of a molecule by luminescence [in $s^{-1}$]. Under these circumstances:

$$L_{sat} = kn_{sat}, \; L'_{sat} = kn'_{sat}, \text{ and } \Delta L = k(n'_{sat} - n_{sat}) \quad \text{(v)}$$

Thus, under saturating conditions, the only event that contributes to a difference in signal is a change in the number of interacting molecules.

The other assumption implicit in the analysis that gave rise to Equations (i) through (iv) is that, under any given set of experimental conditions, the number of molecules producing luminescence is constant. In practice the population of luminescing molecules is expected to be depleted through photodecomposition. Photodestruction quantum yields of typical fluorophores have been shown to be about $10^{-5}$ [Mathies and Stryer, *Applications of Fluorescence in the Biomedical Sciences*, 1986, pp.129-140]. That is, such a fluor emits on the average about $10^5$ photons before it is destroyed. Consequently, the number of molecules producing luminescence will decline exponentially. This population decline will limit the incident radiant power or the duration (or both) of any practical measurement. Indeed, the photodecomposition of fluorophores will fundamentally constrain the total luminescence output and the confidence level of an AML measurement.

In accordance with the subject methodology, a light source, usually monochromatic, is modulated in a light path directed to the sample. Energy of the light source may or may not result in significant photodecomposition of the chromophore (fluorophor or phosphor) to be measured during the period of detection. Light sources are modulated by changing cross-sectional area on which the irradiation impinges, desirably also varying the site at which the light impinges on the sample. The irradiation of the sample in two or more modes will be repeated during the period of measurement. The greater the number of cycles, the smaller the signal which can be detected. The total number of cycles may be as few as one but will usually be at least 100, usually in the range of 1000 to $10^6$. Thus, the irradiated area may be alternately expanded or contracted, and desirably moved from one locus to another. In changing the area which is irradiated, the photon flux remains constant or is normalized, so that the signal which is produced ideally would solely vary with the difference in the number of luminescent moieties per unit volume between the two irradiation sites.

The incident light will be selected t excite the luminescent moieties present in the sample, so as to induce light emission. The light emitted from the sample is collected and directed to a detection system, which receives alternate signals from each measured locus.

Durations of illumination will generally range from about 10 $\mu$sec to 20 millisec, usually 50 $\mu$sec to 10 millisec, where the frequency will generally range from about 10 to 1200 cycles/min. The total period of time for a single measurement of a sample will generally be in the range of about 0.01 to 2 min. The cross-sectional area ratio for the two irradiated areas covering the same center will vary depending on analyte concentration, generally being in the range of about 1:10,000. The volume illuminated will generally be in the range of 0.1 $\mu$l to 1 ml.

Various sources of excitation light may be employed. Examples of monochromatic light sources are lasers, filtered broad spectrum lamps or lamp monochromator systems. A convenient laser light source is illustrated be a 20 mW CW line output operated at 488 nm or 514 nm or a laser that radiates at even longer wave lengths.

In order to modulate the irradiance, the focus of the optical beam may be altered at the sample by moving the source, sample or lens system, by masking with a rotating disk, or by positioning the source beam alternately onto and off of a locus (or loci) of the sample. Various techniques may be employed to vary the locus of the light beam and site of irradiation of the samples.

For measuring the emitted light a discriminating, high efficiency collection detection system is employed. This includes any system which optimally discriminates against Raleigh and Raman photons while collecting a large solid angle of emitted radiation and employing a high quantum yield photodetector. The means to extract the signal from the analyte may be a simple comparison of the signal and background signal level or a means employing time correlation such as gated integration, synchronous detection, autocorrelation, comparative photon counting or a combination of these techniques. The emitted photons may be counted over a predetermined time period to obtain a photon flux per unit time at each locus for each measurement.

The method may find use for any analyte which may provide a luminescent signal, usually in conjunction with a labelled conjugate. With fluorescence, desirably, the fluorophore has a high molar absorbance coefficient $(cm \cdot M)^{-1}$ at least about $10^4$, preferably at least about $10^5$ and more preferably at least $10^6$. The number of fluorescent molecules present as a single aggregate or particle will be at least 1, usually at least 5, more usually at least 10, and may be 100 or more, usually not exceeding 500, more usually not exceeding 200, desirably in the range of about one to 100, more usually 5 to 75. A wide variety of fluorescent chromophores are available, which include fluorescein, rhodamine, phycobiliproteins, such as phycoerythrin, umbelliferone, transition metal chelates, such as europium, gadolinium, etc.

Where the analyte is not naturally fluorescent, it may be made so in a variety of ways. Fluorescent particles may be employed (U.S. Pat. Nos. 3,853,987 and 4,3118,707) to which various ligands or receptors are bound, which may bind to the analyte. For example, the protocol may provide for analyte binding to the particle which may then inhibit a fluorescent particle from binding to an affinity column of analyte, analyte bound to a wall of a container, such as a well of a multiwell plate, or the like. Where cells are of interest, fluorescent labeled antibodies may be employed which are specific for a surface membrane protein or sugar on the surface of the cell. In some instances, conditions may be employed which introduce the luminescent moiety into the cell, where the luminescent moiety undergoes a reaction which maintains the luminescent moiety in the cell or changes a non-luminescent reactant to a luminescent product. If desired, the cells may be readily separated from luminescence conjugated receptor by centrifugation, washing, and re-dispersion. However, since the luminescence labeled receptor will be homogenously dispersed in the medium, it will be sufficient to use the sample medium containing the luminescence label receptor conjugate, since any contribution to the luminescence signal of the uncomplexed receptor conjugate will be subtracted as part of the background.

A wide variety of analytes may be determined in accordance with the subject invention, including haptens, antigens, receptors, aggregates, such as viruses, bacterial cells, protista, fungi, cells from vertebrates or invertebrates, or the like. A list of various ligands and receptors may be found in U.S. Pat. No. 4,233,402. Of particular interest as receptors will be antibodies, either monoclonal or polyclonal, preferably monoclonal.

Various protocols may be employed, depending upon the nature of the analyte. For example, if one wished to determine whether a particular cell type existed in blood, one could add fluorescent conjugated antibody to the blood. If desired and the concentration of the target cell permitted, one could dilute the sample to reduce the red blood cell absorption, alternatively, one could remove the red blood cells initially and use plasma or serum.

Various techniques may be employed to identify the size of the volume where inhomogeneities of the fluorophor may be obtained. By knowing the expected concentration range of the analyte, and the absorbance of the luminescent moiety to be detected, the volume to be measured may be calculated. By using appropriate lenses, a distance between the sample and the lens may be modified, changing the focal point and the volume which is irradiated. Thin films of samples may be employed or fine capillaries. By employing thin films or providing for binding to a surface, a system employing total internal reflection may be employed. In this system, the excitation light is shined on the surface opposite from the sample container at an acute angle to provide for total reflection, whereby only fluorophores within close proximity to the surface will be excited and fluoresce.

For the most part, light will be introduced from the side or from above the sample. The volume of the sample will usually be from about 10 to 500 μl, more usually from about 15 to 50 μl. The sample may be a drop, thin film, a volume contained in a shallow dish, or the like. The depth of the sample will generally be from about 1 μm to 1 cm. The sample may be a fixed sample or a flowing sample, preferably fixed.

A general instrument plan will usually involve a monochromatic light source, which directs light to a means to modulate irradiance, from which light is directed to the sample material. The reflected light from the excitation source is usually directed to a beam dump. The emitted light from the fluorophore is collected in a high-efficiency collection device, and passed through appropriate filters to a detection system, which in turn, feeds the signal to a data processing device for detecting the presence of a luminescence signal above background.

A diagrammatic device is depicted in FIG. 1. A laser 1 is used as the excitation source. The laser output is passed through an optical pathway through a beam definition optic 2, which focuses the laser onto sample holder 3. A thin section of sample is mounted on the sample holder. Luminescence radiation is collected by an ellipsoidal mirror 4 and passed through a filter 5 to a detector 6 operated with a power supply 7. The detector output is processed by an amplifier/discriminator circuit 8 prior to being recorded by signal processing-/control electronics 9. F and F' are the two focal points of the ellipsoidal mirror.

Figure 2A:
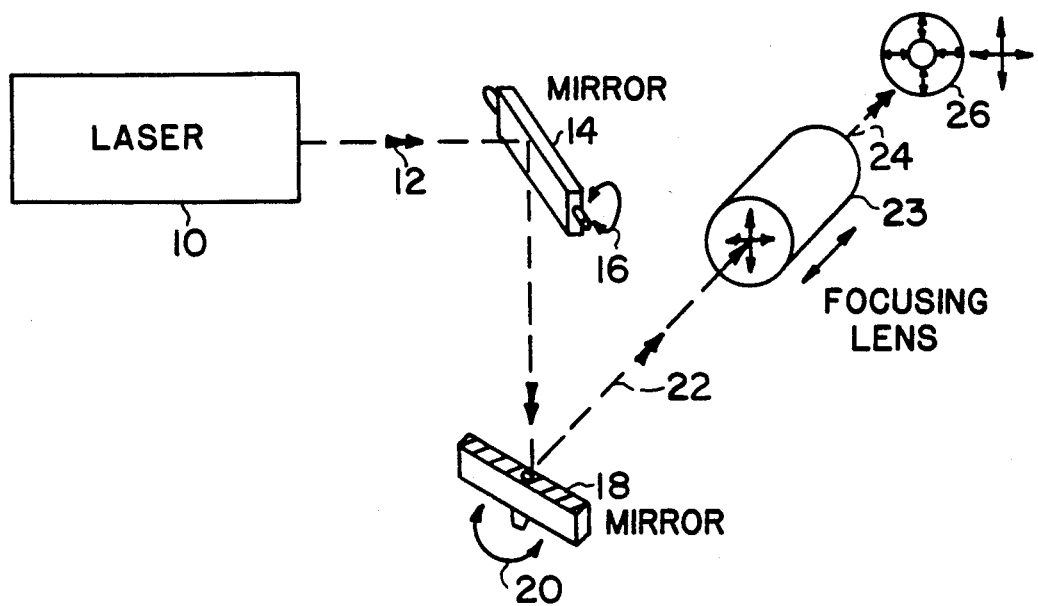
FIG. 2a and 2b are diagrammatic representation of the light system and optical system.

Individual embodiments will now be discussed. The excitation source will normally be monochromatic, have an appropriate wavelength range, and a high enough power to efficiently excite the luminescence. An exemplary source is an argon ion laser operated either at 488 nm or 514 nm. (FIG. 2a depicts a light path for the subject invention):

A laser 10 is used as the light source and the light is transmitted along light path 12 to mirror 14. Mirror 14 rotates along its horizontal axis as indicated by arrow 16. The light is reflected by mirror 14 to mirror 18 which can rotate about its vertical axis as depicted by arrow 20. The light beam path 22 reflected from mirror 20 then passes through focusing lens 23, which is depicted in further detail in FIG. 2b and exits along path 24 to sample 26.

Figure 2B:
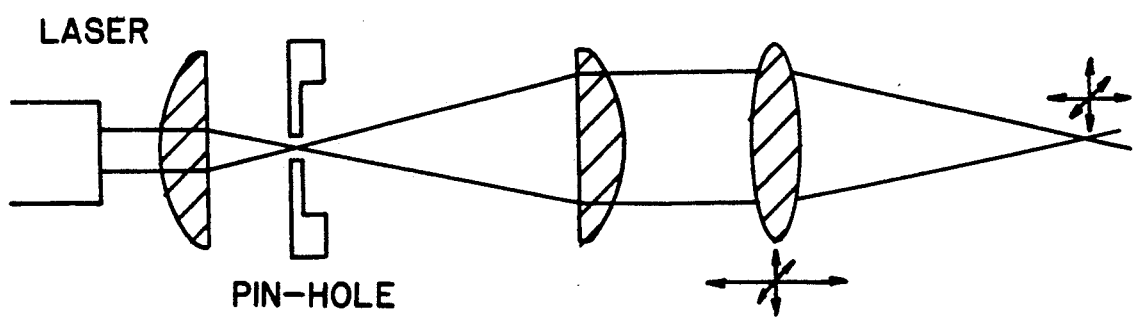

A beam definition optics diagram is depicted in FIG. 2b. A collimated source beam is brought to a focus on the surface of a pinhole $P_1$ by lens $L_1$. These components act as a spatial filter to reduce stray light and improve beam quality. Lens $L_2$ collimates the beam. Lens $L_3$ defines the properties of the beam as it reaches the sample. The lens is mounted on a XYZ stage such as a piezoelectric or stepper motor driven stage. The moveable lens allows for the sample area irradiated by the source beam to be changed, both in terms of the size of the irradiated area and center of the irradiated area.

Alternatively, liquid lenses may be used which can rapidly change their focal length so as to change the area which is irradiated. The technique could employ different lenses on a circulating disk so that the locus and/or cross-sectional area may be changed sequentially.

The collection optic is conveniently an ellipsoidal mirror, which can be an ellipsoid with appropriate openings for the introduction and exiting of the excitation light beam. The ellipsoidal collection optic may be mounted such that the sample area illuminated is at one of the focal points of the ellipse. The excitation beam enters through a small hole in the ellipsoidal mirror. The exit port is centered at the other focal point of the ellipse. By making the optic relatively large (at least about one-half ellipse) and situating the illuminated sample area and exit port at the focal points of the ellipsoidal surface, a major fraction of the luminescence is collected.

The sample holder may be a flat surface, such as a microscope slide or a shallow dish, that holds the sample. The sample is placed on the slide so that it covers an area of approximately 1 cm² (or smaller) and is placed on the slide so that the sample depth is fixed. The surface of the glass slide can be coated with a reflective metal, such as gold, particularly where a double passing through the sample proves advantageous. When this is not done, a beam dump is mounted behind the sample holder. The sample holder may be mounted on an XYZ translation system, as described previously, to effect the illumination of different areas of the sample, when necessary. In the embodiment where the beam is reflected back through the sample, the ellipsoidal mirror will be provided with an exit port for the reflected beam.

The exit port/filter assembly consists of a circular aperture centered at one of the focal points of the ellipsoid and a series of filters. The exit port is the only entrance port to the housing that contains the filter assembly and detector 6. This ensures that only radiation that is produced in the illuminated sample area reaches the detector. The filter assembly is a series of cutoff and band pass filters designed to discriminate against Rayleigh and Raman scattering. Illustrative filters are Oriel Model 53950 band pass filter and Oriel Model 57881 long pass filter.

The detector generally will be an end-on photomultiplier tube (PMT) or photodiode. A PMT will usually have a large photocathode so that high collection efficiency is not dependent on the exact focusing of the luminescence at the second focal point of the ellipse. The PMT can be powered by a stable high voltage power supply 7 and operated in the photon counting mode. A cooled housing may be employed to lessen the effects of PMT dark current.

The amplifier/discriminator 8 receives the output of the PMT and processes the output. The circuits are common and are illustrated by S.I./McPherson Model 7701 Photon Counting System or Hamamatsu Model C1230 Photon Counter with amplifier/discriminator.

The signal processing/control electronic system 9 will have several key components. The entire system is controlled by a microprocessor that, via software, controls the functioning of the instrument and the collection of the data. The output of the amplifier/discriminator circuit is taken to a computer controlled gated counter. The data collected in the counter is stored for later processing. The microprocessor also controls the position of the moveable optic ($L_3$), and as appropriate, the sample holder, or other component of the excitation light path. Using this arrangement, the measurement process can be selected via software, depending upon which method is desired, such as whether a single locus or multiple loci are employed, which are expanded and contracted.

While the subject device provides for internal control, to further ensure that the light source and protection system provide for a substantially constant signal, the original beam may be split and transmitted to a PMT. In this way, by employing choppers, one can alternate the signal from the sample with the signal from the control to maintain a constant value for the device. Various techniques have been employed for providing a correction based on fluctuations in the device. See for example U.S. Pat. No. 4,750,837, as well as other patents indicated previously.

The subject invention provides for a novel technique for accurate determination of the presence of luminescent moieties at extremely low concentration levels. By exploiting the inhomogeneity of the media, sample volumes may be irradiated which have a high probability of having different levels of luminescent moieties. By subtracting the two results, one also subtracts out variations in the equipment used for the measurement and scattered light or luminescence-emitting moieties in the media. In this way, by cycling irradiation from a first to a second locus, with expansion and contraction about a common center, one can obtain a large number of results, which may be averaged so that only a small change in signal may be detected in the presence of a relatively large amount of background noise. The technique finds application in any system where one wishes to detect an analyte which is present at concentrations significantly below nanomolar.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A device comprising:
   an excitation optical system projecting excitation light of a constant radiant power or photon flux at a wavelength or wavelengths selected for a sample into said sample;
   a sample cell for said sample;
   means for alternately irradiating different regions of said sample having different volumes;
   emitted light sensing means sensing the emitted light;
   means for comparing the difference in the emitted light from said regions of different volumes.

2. A device according to claim 1, wherein said excitation optical system comprises a lens for focusing said excitation light on said sample and said means for alternately irradiating comprises means for changing the distance between said sample cell and said lens.

3. A device according to claim 1, wherein said device further comprises means for cycling said alternate irradiation and averaging the emitted light from each of said regions.

4. A device according to claim 1, wherein said emitted light sensing means comprises an ellipsoidal mirror with said sample cell at one focus of said ellipsoidal mirror.

5. A device according to claim 1, wherein said means for comparing comprises an amplifier/discriminator circuit and signal processing/control electronics, which receives signals from said amplifier/discriminator circuit and controls the means for alternately irradiating.

6. A device according to claim 1, wherein said device further comprises means for determining the fluctuations in signals from said alternate irradiation of said different volumes and means for determining the concentration of light emitting sources in said sample by means of differences in said fluctuations.

* * * * *